United States Patent [19]

Caldarise

[11] Patent Number: 5,641,323
[45] Date of Patent: Jun. 24, 1997

[54] SELF-LUBRICATING IMPLANTABLE ARTICULATION MEMBER

[75] Inventor: Salvatore Caldarise, Hanson, Mass.

[73] Assignee: Johnson & Johnson Professional, Inc., Raynham, Mass.

[21] Appl. No.: 589,598

[22] Filed: Jan. 16, 1996

Related U.S. Application Data

[63] Continuation of Ser. No. 198,996, Feb. 18, 1994, abandoned.
[51] Int. Cl.$^6$ ........................................... A61F 2/30
[52] U.S. Cl. ..................... 623/22; 623/11; 623/16; 623/18; 623/23
[58] Field of Search .................. 623/11, 16, 18–20, 623/22–23

[56] References Cited

U.S. PATENT DOCUMENTS

| | | |
|---|---|---|
| 3,528,109 | 9/1970 | Scales . |
| 3,605,123 | 9/1971 | Hahn . |
| 3,723,995 | 4/1973 | Baumann ............................ 623/22 |
| 3,818,512 | 6/1974 | Shersher ............................ 623/22 |
| 4,032,994 | 7/1977 | Frey ................................... 623/23 |
| 4,281,420 | 8/1981 | Raab . |
| 4,314,381 | 2/1982 | Koeneman . |
| 4,318,191 | 3/1982 | Tepic ................................... 623/23 |
| 4,365,359 | 12/1982 | Raab . |
| 4,722,870 | 2/1988 | White . |
| 4,770,659 | 9/1988 | Kendall .............................. 623/22 |
| 4,781,721 | 11/1988 | Grundei . |
| 5,201,738 | 4/1993 | Scott et al. . |
| 5,204,055 | 4/1993 | Sachs et al. . |

FOREIGN PATENT DOCUMENTS

| | | | |
|---|---|---|---|
| 2742464 | 3/1979 | Germany ............................ 623/18 |
| A-0084094 | 7/1983 | Germany . |
| 1519687 | 11/1989 | U.S.S.R. ............................. 623/22 |
| 2080118 | 7/1981 | United Kingdom . |

OTHER PUBLICATIONS

Francis W. Cooke, Ph.D., "Ceramics in Orthopedic Surgery", Clinical Orthopaedics and Related Research, Dec. 7, 1990.

Gavrjushenko, "Recommendations with Respect to the Improvement of Lubricating Qualities of Synovial Fluid in Artificial Joints", 2267 *Proceedings of the Institution of Mechanical Engineers*, 207 (1993) No. H2, Part H, London, GB.

Copy of European Search Report dated Jul. 6, 1995.

*Primary Examiner*—Michael J. Milano
*Assistant Examiner*—P. Zuttarelli
*Attorney, Agent, or Firm*—William C. Geary, III; Nutter, McClennen & Fish, LLP

[57] ABSTRACT

Implantable articles, such as bone prostheses, are prepared by casting techniques and have incorporated therein fluid communicating passageways. The internal fluid communicating passageways convey synovial fluid from a joint space to the articulation surface of an artificial joint. The presence of synovial fluid at the articulation surface provides sufficient lubricity to the joint and enables artificial joints to utilize metal/metal, metal/ceramic, and ceramic/ceramic articulation couples without the need for a low friction polymeric lining material. Accordingly, artificial joint components formed according to the present invention are less likely to develop wear debris. The implantable articles are formed by a casting process from casting molds that are prepared using a three dimensional printing technique.

25 Claims, 3 Drawing Sheets

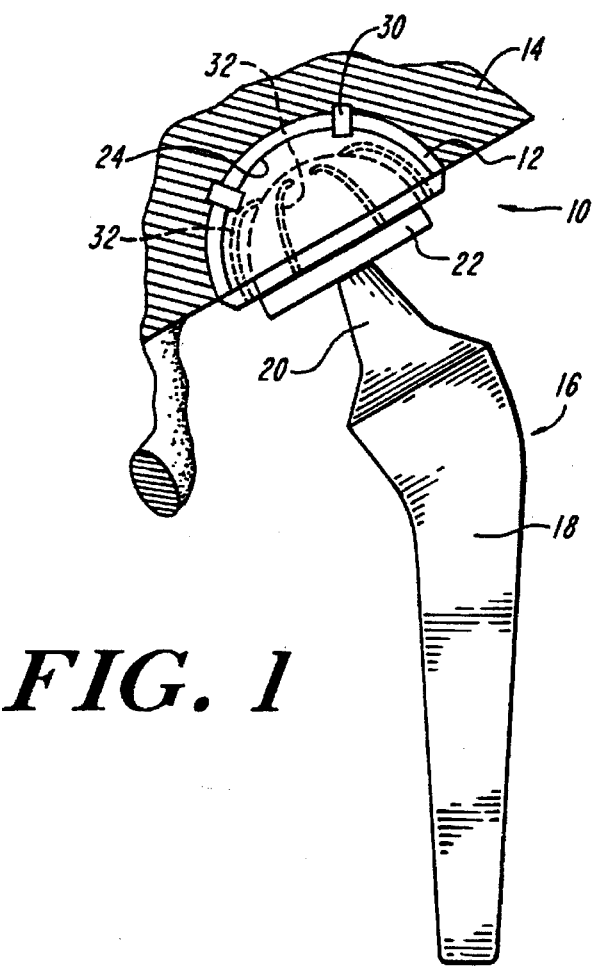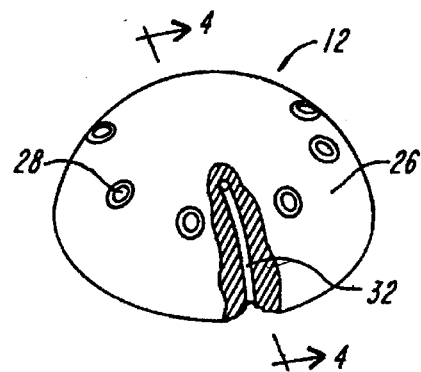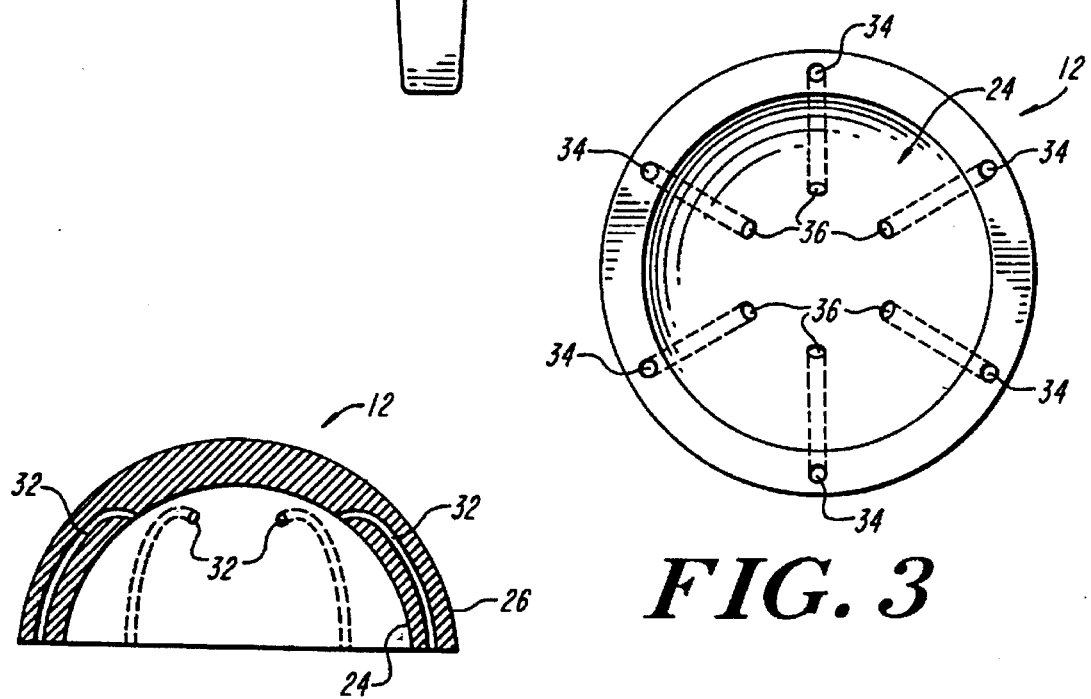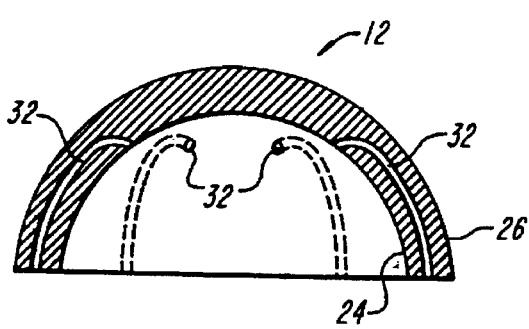
FIG. 1
FIG. 2
FIG. 3
FIG. 4

SELF-LUBRICATING IMPLANTABLE ARTICULATION MEMBER

This application is a continuation of application Ser. No. 08/198,996 filed on Feb. 18, 1994 Entitled: SELF-LUBRICATING IMPLANTABLE ARTICULATION MEMBER, now abandoned.

The invention relates to implantable bone prostheses. More particularly, the invention relates to self-lubricating bone prostheses that serve as articulation members in artificial joints.

Joint replacement surgery is quite common and enables many individuals to function normally when otherwise it would not be possible to do so. Artificial joints are normally composed of metallic or ceramic components that are fixed to existing bone.

Artificial hip joints, for example, include several components. A femoral component of an artificial hip comprises an elongate stem or shaft at its distal end that is affixed within the medullary canal of the femur. A proximal end of the stem includes neck region, to which is attached a femoral head. The acetabular shell is a separate component of an artificial hip joint that is affixed within existing bone such as the acetabulum. The acetabular shell includes a cup-like region that receives the femoral head. The femoral head and the acetabular shell form an articulation couple and smooth low frictional movement of the femoral head within the shell is essential to ensure proper functioning of the artificial hip joint.

Artificial knee joints include a tibial plateau that is mounted to the tibia and a knee femoral that is mounted to the femur. The tibial plateau and the knee femoral form the articulation couple of an artificial knee joint. In a properly functioning artificial knee joint, the knee femoral must slide freely over the adjacent surface of the tibial plateau.

Metal to metal articulation couples are often used in artificial joint construction and at least one of the articulation members is coated with a low friction polymeric material. A common low friction polymeric coating that is applied to an articulation surface of an articulation member is ultrahigh molecular weight polyethylene (UHMWPE). UHMWPE is a durable polymer that has a very low coefficient of friction and enables smooth movement of the two components over each other.

Natural friction within a replaced, artificial joint can cause minute particles of debris (e.g., metal from the joint or polymeric liner material) to become dislodged and to migrate within the joint. The phenomenon of wear debris within artificial joints is a serious problem that can inhibit the proper mechanical functioning of the joint. Wear debris can also lead to osteolysis and bone deterioration. If wear debris develops within an artificial joint it must usually be corrected by surgical removal of the debris or by subsequent replacement of the artificial joint.

The articulation couple of artificial joints is believed to be the principal source of wear debris. Currently, the state-of-the-art articulation couple in an artificial hip joint, for example, is a cobalt-chromium femoral head seated within a cobalt-chromium acetabular shell that is lined with UHMWPE. Despite this being one of the more advanced articulation couples, significant wear debris is believed to result from erosion of the polyethylene liner material.

Metal/metal articulations are generally preferred because of their strength. However, a polymeric liner material is generally necessary to reduce friction in the joint, and these liner materials often contribute to wear debris. Current technology has not permitted the use of metal/metal articulations without a low friction liner material.

Ceramic/ceramic articulation couples are believed to be potentially useful in artificial joints. Their actual use in artificial joints is, however, very limited because of the inherently low tensile strength of these materials. Ceramic materials are also quite brittle and their use as orthopedic implants, in load bearing applications, is further limited due to the risk of unpredictable catastrophic failure. See, Cooke, Clinical Orthopaedics and Related Research, 276:135–146 (1992). The practical use of ceramic/ceramic articulation couples also poses additional challenges with respect to fixation within bone and the manufacture of joint components having complex shapes.

Accordingly, there is a need for articulation couples of artificial joints that combine excellent mechanical and frictional properties while reducing or eliminating the problem of wear debris.

It is thus an object of the invention to provide a suitable strong and effective low friction articulation couple for artificial joints. Another object of the invention is to provide an articulation couple that greatly reduces or eliminates the tendency for wear debris to form within an artificial joint. A further object is to provide an effective metal/metal articulation couple for an artificial joint. It is also an object of the invention to provide an metal/metal articulation couple for an artificial joint that is self-lubricating. Other objects will be apparent from the description that follows.

SUMMARY OF THE INVENTION

The present invention provides implantable components of artificial joints that have improved lubrication properties. The invention is particularly applicable to articulation members of artificial joints that have improved articulation couples. Artificial joints constructed with the articulation members of the invention have articulation couples that are less likely to contribute to wear debris within the joint.

Articulation members of the invention include a bone-engaging surface that enables the member to be fixed within existing bone and an opposed articulation surface that abuts the articulation surface of another articulation member of the joint at the wear surface of the joint. In a properly functioning artificial joint, relative motion occurs between the two adjacent articulation members at the wear surface.

The articulation members of the invention are designed to be self-lubricating at the articulation or wear surface of the joint by enabling synovial fluid naturally present within a joint capsule to be conveyed to the articulation surface of one or both of the adjacent articulation members. At least one primary internal passageway is disposed within the articulation member to transport the synovial fluid to the wear surface of the joint. Preferably, the primary internal passageway originates at an inlet port on a side of the member that is adjacent the joint space.

In one embodiment the primary internal passageway terminates within the articulation member and communicates with one or more secondary internal passageways. The secondary passageways, in turn, communicate with one or more outlet ports disposed on the articulation surface of the member. Alternatively, one or more primary internal passageways can extend directly from the inlet port adjacent the joint space to an outlet port disposed on the articulation surface of the member.

The internal passageways are oriented within the articulation member such that they do not compromise the strength of the member and so that fluid flow within the passageways is not inhibited. The primary and secondary internal passageways are of a relatively small diameter that is sufficient for fluid to be passed through the passageways by capillary action. Generally the diameter of the passageways is in the range of 0.005 to 0.100 inch.

The internal passageways formed in the implantable article of the invention enable the articulation member to have a self-lubricating articulation surface. The synovial fluid that is conveyed through the passageways from the joint space provides sufficient lubricity to the articulation surface to allow proper functioning of the joint. Moreover, artificial joint components constructed according to the present invention may utilize metal/metal or metal/ceramic articulation couples without the need for coating the articulation surface of at least one or the articulation members with a low friction polymer such as UHMWPE. The absence of any such coating is believed to significantly reduce the incidence of wear debris within the joint.

The implantable articles of the invention can be manufactured by suitable casting techniques. Preferably, however, the casting molds used in the casting process are prepared through a three-dimensional (3-D) printing process. The use of 3-D printing enables the manufacture of ceramic or ceramic forming molds having small diameter internal passageways that are positioned in a desired location.

The 3-D printing process used to form casting molds according to the present invention generally includes the steps of manufacturing a mold surface by building up the surface of the mold one layer at a time. A powder material of suitable composition is deposited layer by layer, and a portion of each layer is solidified by applying a binder material in select regions thereof. In this manner a green mold is prepared, after which it is dried and fired. After firing the mold is condition to accept molten metal during the casting process.

During the 3-D printing process mold regions that define an internal passageway are prepared by forming a solid region of mold material at a location corresponding to the desired placement of the passageway. Once a molten metal is poured into the mold to form the implantable article, the metal will envelop the ceramic mold regions that correspond to the internal passageways. After removal of the ceramic mold material an open passageway will correspond to the location of the solid region of the ceramic mold material.

BRIEF DESCRIPTION OF THE DRAWINGS

FIG. 1 is a perspective view illustrating an artificial hip joint having an acetabular shell, affixed within the pelvic bone, and a hip femoral component mounted within the acetabular shell.

FIG. 2 is a perspective, partially cut away view of an acetabular shell constructed according to the present invention.

FIG. 3 is a bottom view of the acetabular shell of FIG. 2.

FIG. 4 is a sectional view of the acetabular shell of FIG. 2 at lines 4—4.

DETAILED DESCRIPTION OF THE INVENTION

Figure 6:
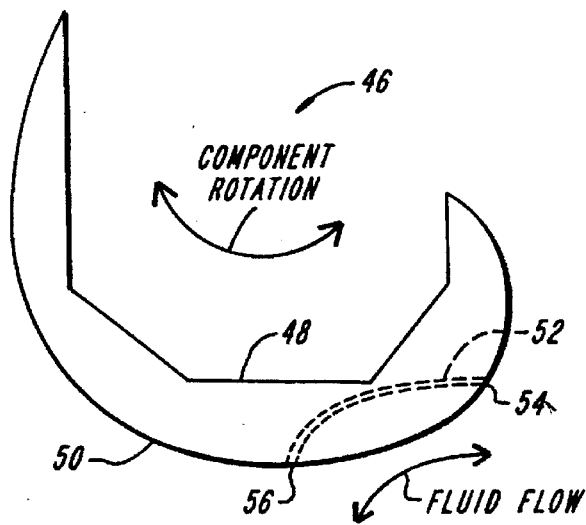
FIG. 6 is a side view of a knee femoral constructed according to the present invention.

The invention relates to self-lubricating implantable articles. Preferably, the implantable articles are bone prostheses such as articulation members of artificial joints. The self-lubricating properties of the implantable articles help to ensure a properly functioning joint.

Accordingly, the implantable articulation members of the invention are constructed such that synovial fluid is drawn to the articulation surfaces of the members through internal passageways disposed in the members. The synovial fluid thus provides sufficient lubricity at the articulation or wear surface of two adjacent articulation members. This self-lubricating feature enables the use of articulation couples in artificial joints, such as metal/metal and metal/ceramic, while eliminating the need to line all or a portion of the articulation surface with a polymeric material.

One particular advantage offered by the present self-lubricating implantable articles is the elimination of the need to use polymeric liner materials, such as UHMWPE, at the articulation surface of an artificial joint. Artificial joints thus formed without such a liner material are less prone to develop wear debris. The synovial fluid conveyed to the articulation surface of the joint provides sufficient lubricity to enable metal/metal articulation couples to be used effectively in an artificial joint without a liner material.

FIGS. 1 through 4 illustrate an artificial hip joint 10, and various components thereof that are constructed according to the present invention. Artificial hip joint 10 includes an acetabular shell 12 that is fixed within existing bone of the acetabulum.

FIG. 1 illustrates a femoral hip stem 16 and femoral hip head 22 articulate within the acetabular shell 12. The hip femoral 16 includes an elongate distal stem 18 and a proximal neck region 20. A femoral head 22 is secured to the neck region 20 of the hip femoral 16. As illustrated, the femoral head 22 fits within the acetabular shell 12. Relative motion occurs between the femoral head 22 and the inner surface 24 of acetabular shell 12. Thus, surface 24 and head 22 form the articulation surfaces of the artificial hip joint. Accordingly, the femoral head 22 is able to articulate freely within the acetabular shell 12 without dislocating the joint.

FIGS. 1 through 4 best illustrate the construction of self-lubricating implantable articles according to the present invention, in the context of a self-lubricating acetabular shell. Acetabular shell 12 incudes an external bone-engaging surface 26. Preferably, surface 26 is irregular and may include screw holes 28 for seating bone screws 30. The acetabular shell has one or more internal fluid conveying passageways 32 that are disposed between the external surface 26 and the internal surface 24 of the acetabular shell. Passageways 32 are designed to communicate synovial fluid from a joint space, adjacent to inlet ports 34, to be discharged through outlet ports 36 that are formed on the inner or articulation surface 24 of the acetabular shell 12. The outlet ports 36 are positioned to deposit the synovial fluid at the articulation surface of the articulation members of the joint.

Figure 5:
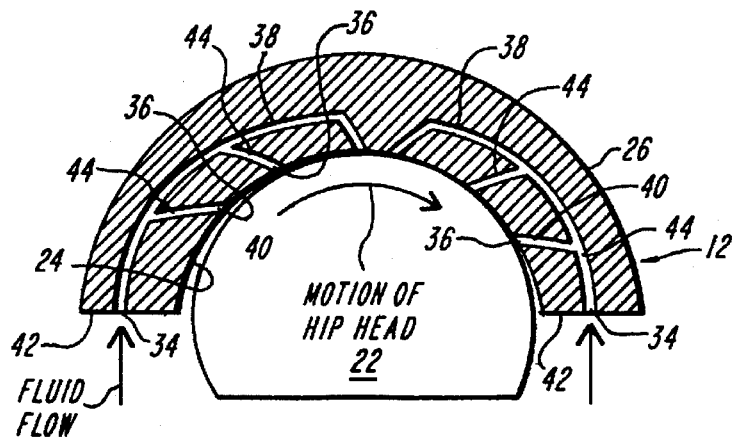
FIG. 5 is schematic view illustrating the mounting of a hip head within an acetabular shell constructed according to the present invention.

FIG. 5 illustrates one embodiment of the invention in which the implantable article, such as acetabular shell 12, includes primary internal passageways 38 and secondary internal passageways 40. As illustrated, primary internal passageways 38 communicate fluid through the passageway 38 from an inlet port 34 on a surface 42 of acetabular shell 12 that is adjacent to a joint space. Secondary internal passageways 40 communicate fluid between fluid communication ports 44 on the primary passageway and outlet ports 36 disposed on the internal surface 24 of the acetabular shell 12. In the embodiment illustrated in FIG. 5 two separate and independent primary passageways 34 communicate fluid from the joint space to separate secondary passageways 40.

Figure 7:
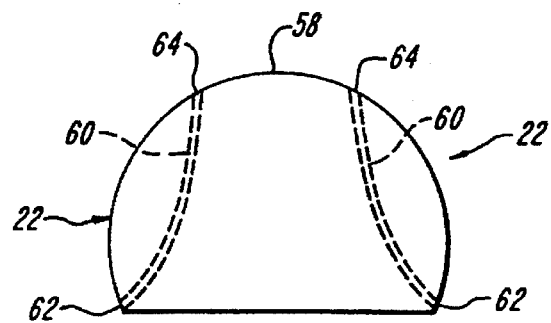
FIG. 7 is a side view of a hip head constructed according to the present invention.

The invention is also applicable to self-lubricating implantable articles useful as articulation members in a variety of other artificial joint components. FIGS. 6 and 7 respectively illustrate self-lubricating knee femoral 46 and a self-lubricating femoral head 22.

FIG. 6 illustrates a knee femoral 46 that is affixed at bone engaging surface 48 to a distal end of the femur (not shown). The articulation surface 50 of knee femoral 46 abuts a tibial plateau (not shown) that forms another articulation member of an artificial knee joint. Together, the articulation surface 50 of the knee femoral 46 and a corresponding articulation surface of a tibial plateau form the articulation surfaces in an artificial knee joint. Knee femoral 46 includes internal fluid communicating passageway 52 that communicates synovial fluid from inlet port 54, adjacent to a joint space, through outlet port 56 to be deposited at the interface between the articulation members. Although not illustrated, one or more secondary passageways may communicate fluid from passageway 54 to various locations on articulation surface 50.

As illustrated in FIG. 7, femoral head 22 includes an articulation surface 58 which is operatively disposed within acetabular shell 12. One or more passageways 60 extend from an inlet port 62, adjacent to a joint space, to outlet ports 64 on the articulation surface 58. Passageways 60 communicate synovial fluid from the joint space internally through the passageways in the femoral head to deposit the synovial fluid at the interface of the articulation surface 58 of the hip head 22 and the inner surface 24 of the artificial hip joint.

It is understood that the self-lubricating implantable articles of the present invention may be used with a variety of bone prostheses in addition to those illustrated above. Such constructions for implantable articles are applicable to articulation members used in other artificial joints, including artificial shoulders, fingers and elbows.

Synovial fluid is normally present within the joint capsule of individuals. The self-lubricating implantable articles of this invention exploit the lubricating properties of synovial fluid and provide passageways to communicate the synovial fluid to the articulation surface of an artificial joint. The synovial fluid thus facilitates a high degree of lubricity between articulation members of artificial joints so constructed.

The dimensions and orientation of the fluid communicating passageways will vary depending upon the joint component on which they are formed. Generally, the passageways are constructed to fit within the dimensions of the implantable article without compromising its strength. The passageways should also be constructed to have smooth internal walls and to be spatially oriented within the implantable articles so as to facilitate the smooth and continuous flow of fluid therethrough by capillary action. Thus, the passageways should not include any abrupt changes of direction or severe angles. Moreover, the passageways preferably have a circular cross section.

The passageway geometry is also defined, to some extent, by the properties of the synovial fluid. Significant properties of the synovial fluid include the surface tension and wetting angle of the synovial fluid, both of which are a function of temperature. The surface tension properties and wetting angle properties of the fluid are also dependent upon the material from which the passageways are formed. Using the properties of surface tension and wetting angle, a suitable internal passageway diameter that results in appropriate pressure differential between the inlet and outlet of the passageway can be estimated according to the equation $$p = \frac{4\sigma|\alpha|}{D}$$

where p represents pressure, D represents the diameter of the passageway, $\sigma$ represents surface tension, and $\alpha$ represents contact angle.

In one embodiment passageways formed within an acetabular shell originate at an inlet port disposed on the rim of the acetabular shell adjacent to a joint space. The passageways extend internally within the shell between the bone-engaging surface and the articulation surface of the acetabular shell. The passageways, as noted above, can terminate in outlet ports disposed on articulation surfaces, or they can communicate with separate, secondary passageways that communicate with outlet ports disposed on the articulation surface. Acetabular shells, for example, normally have a wall thickness (the distance between the articulation surface and the bone-engaging surface) that ranges between about 0.150 inch and 0.300 inch. The diameter of fluid communicating passageways disposed within such an acetabular shell would normally be in the range of about 0.005 inch to 0.100 inch. A preferred passageway diameter is in the range of about 0.007 inch to 0.040 inch. The length of the internal passageways is, of course, dictated by the dimensions of the implantable articles within which they are disposed and the orientation of the passageways within the implantable articles.

As illustrated in FIGS. 6 and 7, fluid communicating passageways formed in knee femorals and femoral heads are generally arcuate. Like passageways formed in the acetabular shell, the orientation and dimensions of passageways disposed in knee femorals and femoral heads will depend upon the size of the implantable article in which they are formed. The diameter of such passageways likewise is in the range of approximately 0.005 to 0.100 inch. A preferred diameter is in the range of about 0.007 inch to 0.040 inch.

As noted above, the self-lubricating implantable articles of the present invention are constructed to communicate synovial fluid from the joint space to the articulation surfaces of an artificial joint. As the joint undergoes its normal motion, synovial fluid is drawn into the inlet port of the passageway. Continued motion of the joint causes additional fluid to be drawn within the passageway. Eventually, the fluid traverses the passageway and is deposited at the articulation surface of the joint.

FIG. 6 illustrates that component rotation of the knee femoral 46 of an artificial knee joint in the direction illustrated causes fluid flow to oscillate back and forth within channel 52. Continued motion of the joint thus provides a supply of synovial fluid at the wear surface of the joint to provide sufficient lubricity and to facilitate proper functioning of the joint.

The material that forms the inner surfaces of the internal passageways should be one that has a relatively low wetting angle such that fluid spreads over the surface of the passageway to promote fluid communication by capillary action. Biocompatible materials with low wetting angles are among the most preferred. Exemplary materials include cobalt-chromium alloys such as ASTM F-75 from which the implantable article itself is made.

Implantable articles that include internal fluid communicating passageways as described above pose significant manufacturing challenges due to the intricate internal geometries involved. A preferred method of manufacturing such implantable articles is to utilize a computer controlled three dimensional ("3-D") printing technology to manufacture casting molds for directly casting the implantable articles. The casting molds can then be used to cast implantable articles that include integral, as-cast internal fluid communicating passageways of the type described above.

The 3-D printing process applicable to the preparation of casting molds for implantable articles of the type described herein utilizes loose powder that is applied in successive layers, with binder selectively applied to each layer by a computer controlled scanning nozzle similar to an ink jet. The application of binder to the powder layers selectively solidifies the powder in each layer in a region or profile corresponding to a section of the desired three dimensional solid. Suitable three dimensional printing techniques for the practice of the invention are disclosed in U.S. Pat. No. 5,204,055 to Sachs, et al., which patent is hereby expressly incorporated by reference.

The process involves the deposition of a layer of a powder material in a confined area and the application of a binder material to selected regions of the powder layer to solidify the powder in desired regions. A next layer of powder is then deposited over the first layer, and binder material is again applied to selected, generally partially overlapping regions of the second layer of powder to solidify the second layer in new regions and to bind the solidified sections to the previously solidified sections of the first layer. These steps are repeated according to a predetermined pattern to obtain an object formed of many successive laminations of powder and binder material. The regions in which binder material is deposited in each scan layer correspond to the sections, at the current scan height, of the three dimensional object being formed. As further described below, the object to be formed preferably is a mold surface, which may be either an open or a closed mold surface. By "closed" mold surface is meant a cup-shaped cavity, into a which a complimentary-shaped article may be cast. By "open" mold surface is meant a curved or flat plate which is not intended, in and of itself, to receive a casting medium, but which may be incorporated into a mold cavity to impart a surface shape to an object cast therein.

Three dimensional printing processes are generally computer controlled. Virtually any design that can be scanned or interpreted by a computer may be reproduced, regardless of its complexity, subject to the resolution limit of a 3-D printing apparatus. Resolution for a powder consolidated 3-D printer discussed below currently can prepare structures with surface details as small as about 0.007 inch. However, further process improvement may reduce this value.

Casting molds formed by the present invention represent negatives of implantable articles to be cast. Accordingly, solid, generally cylindrical and elongate structures are incorporated into the mold. These solid, cylindrical regions correspond to the internal fluid communicating passageways that are to be formed within cast implantable articles. The solid, cylindrical regions would normally span from a rim of the mold, corresponding to a surface of the implantable article that will be placed adjacent to a joint space, to a surface of the mold that corresponds to the articulation surface of the cast implantable article.

A preferred 3-D printing apparatus useful in practicing the present invention is available from Solizen, Inc. of Northridge, Calif. as model DSPC-alpha version.

Figure 8A:
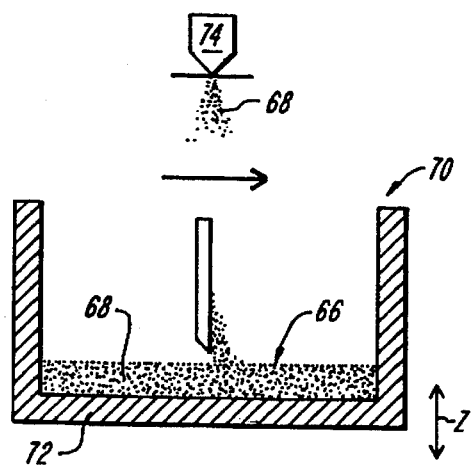
FIGS. 8A through 8C sequentially illustrate a method of manufacturing a mold for an acetabular shell according to the present invention.
Figure 8B:
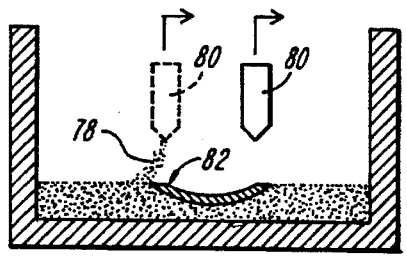
Figure 8C:
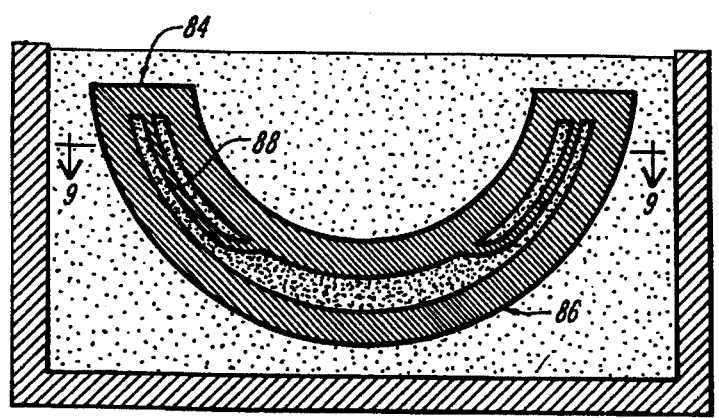

A method of making a mold for an implantable article according to the present invention is illustrated in FIGS. 8A through 8C. The process begins with the deposition of a layer 66 of a powder material 68 in a confined region 70 as shown in FIG. 8A. The confined region 70 is defined on the surface of a stage or platen 72 which is moveable in a feed direction, indicated by axis z, perpendicular to the plane of the platen. Motion along the feed direction allows the platen 72 to receive additional layers of powder material or, alternatively, it permits removal of the finished part. The powder material is deposited in a very thin layer within a contour in the confined region which is preferably selected to encompass either a longitudinal or transverse cross section or profile of a mold for forming the desired implantable bone prostheses. Each layer of powder 66 is preferably about 0.007 inch thick and the powder is deposited so that it is relatively loosely spread. Preferably, powder is deposited from a powder dispensing mechanism 74 that is disposed over the confined region 70. A leveling device (not shown), such as vibrating rollers, can be activated to smooth out the powder layer or to assure that the layer has uniform thickness, preferably of about 0.007 inch.

The powder material may be any material which is capable of being solidified upon the application of a binder to form a casting mold. Typical powder materials used in the method of the invention are ceramic-forming materials, such as alumina, silica, silicon carbide, silicon nitride, zirconia powders, and other materials and mixtures thereof. The powder material can be mixed with materials that act as fluxes or mold conditioners, such as are generally employed in making ceramic molds for casting techniques. Suitable materials are described in U.S. Pat. No. 5,204,055 (Sachs, et al.).

As shown in FIG. 8B, after deposition of the uniform unconsolidated powder layer 66 a binder material 78 is deposited onto selected regions 82 of the powder layer 66 according to a pattern which is defined by the desired cross section of dimensions of the implantable article at a given location and the structural features to be incorporated into the article. Preferably, the binding material 78 is dispensed from a deposition mechanism 80 that operates in a manner similar to an ink jet print head. The deposition mechanism 80 preferably has relatively fine resolution that is appropriate for the level of complexity and detail to be attained in the article to be cast from the mold.

The deposition mechanism 80 is controllably scanned, e.g., by an appropriate carriage and step or drive, over the powder area to define an image-wise pattern 82 of binder material 78. As with conventional image-printing techniques, the deposition mechanism 80 may include means for adding a microdeflection or offset to the liquid nozzle so as to effectively print with half-dot resolution.

The binder material 78 may be any organic or inorganic binder material which will wet or react with and solidify the powder material 68 to which it is applied. Typical binder materials include cellulosic resins, butyral resins, polycarbosilazane and silicate-based materials, and other liquids normally used as binders for forming ceramic molds. Aqueous colloidal silica is a presently preferred binder material for applications that require the powder to be solidified and fired into a solid ceramic.

The powder deposition and binder material application steps of FIGS. 8A and 8B are repeated as each powder layer is solidified in the selected regions according to a predetermined scan actuation pattern. The platen 72 is moved along the z axis perpendicular to the plane of the platen by a distance equal to the thickness of the powder layer 66 with each scan to permit the deposition of a new powder layer and application of binder material to the new layer. The solidified sections of each successive layer are bonded to at least a portion of the solidified regions in the powder layer immediately below so that the entire multi-layer deposition and scan process defines a single, continuous three dimensional object composed numerous thin ring-laminations of powder material to form a solid shell. In this manner a complete mold 84, as shown in FIG. 8C, is prepared.

In the exemplary process illustrated in FIGS. 8A–8C alumina powder is used to form layers 66 and silica is used as the pattern solidifying binder material 78. A green (i.e., unfired) casting mold 86 is prepared in the form of the negative image of an acetabular shell in which an implantable acetabular shell may be formed.

Figure 9:
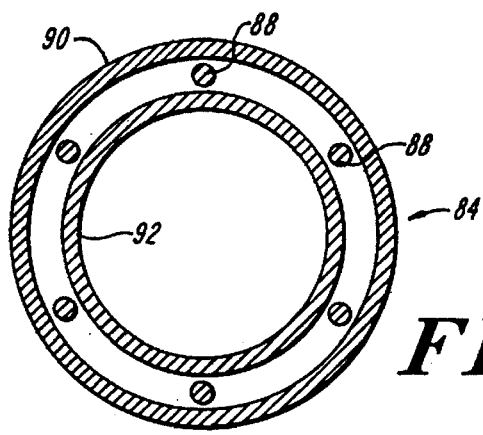
FIG. 9 is a bottom view a mold of an acetabular shell prepared according to the present invention.

FIG. 9, which is a sectional view of the mold 84 shown in FIG. 8C along lines 9—9, illustrates that the mold has incorporated therein solidified cylindrical regions 88 that correspond to fluid communicating passageways that will be formed in the cast article. Solidified, cylindrical regions 88 are disposed in the mold 84 between the outer wall 90 and the inner wall 92 of the mold. When the casting mold is filled with molten metal or metal alloy, the metal cools and conforms to the shape of the mold. Elongate, regions of ceramic that correspond to the internal passageways remain in the cast article. Upon fracturing the mold to remove the cast article the solid, elongate ceramic regions are likewise removed, thus leaving behind a passageway in the form of a void.

The 3-D printing techniques described herein enable the mass production of casting molds that correspond to the shape of implantable articles and which include internal regions that represent negatives of fluid communicating passageways to be formed in the implantable articles. The casting molds are mass produced directly out of ceramic or ceramic forming materials, with the casting mold constructed layer by layer in a 3-D printing process. This process thus avoids the need to make a solid model of the desired object, within which it would be difficult to incorporate the internal fluid communicating passageways. The printed mold of FIGS. 8 through 9 is used to cast a metal implantable article, such as a bone prosthesis, and the mold may be removed from the prosthesis without damaging the cast metal prosthesis. Ultrasonic fracturing and solvent removal are examples of techniques that may be used to selectively remove the ceramic material without attacking the cast metal article. These techniques assure that there is no risk to the delicate and or complex surface geometries of the molded object and its internal fluid communicating passageways.

Once the mold 84 is printed, loose powder material 68 which is not solidified or bonded within the casting mold is removed from about the casting mold. The mold may be shaken to dislodge and remove loose powder, or it may be immersed in a bath or solvent in which the loose powder material is washed away or dissolved while the solidified portions of the mold remain. Loose powder material which is difficult to remove completely because of its location within the casting mold may be more readily removed by subjecting the casting mold to ultrasonic or other high frequency vibration, followed by or concurrently with immersion in a bath or solvent. Ultrasonic vibration and/or immersion in a bath or solvent are techniques that are particularly useful to remove confined loose particles, such as within or adjacent to the solidified, cylindrical regions 88.

Leaching agents such as sodium hydroxide can also be used to attack and remove ceramic materials without affecting the metal material. Such leaching agents can be particularly effective to remove ceramic from within elongate ceramic regions that correspond to the internal passageways.

After loose powder is removed from the casting mold, the hollow casting mold is preferably baked to dry off volatile material, and fired in a furnace at a suitable temperature for a sufficient period of time to yield a strong ceramic mold. A preferred powder material for forming the mold is alumina which, when solidified with an application of aqueous colloidal silica as binder material, may be fired at a temperature of about 1925° F. for approximately two hours to form a fired alumina casting mold. The fired casting mold is strong and thermally stable so that it defines a precise mold cavity.

Depending upon the degree of ceramic consolidation that is desired for proper mold strength, a certain amount of shrinkage may be expected upon firing the green ceramic. Accordingly, those having ordinary skill in the art will readily appreciate that mold shrinkage can be compensated for by forming molds enlarged by a scale factor over the size of the article which is ultimately to be cast therein. Preferably, the molds have dimensions that are approximately 1 to 2 percent larger than the dimensions of the article to be cast.

After firing, the hollow mold 84 receives a molten metal or metal alloy which is allowed to solidify within the mold to form the desired the object. Suitable metal alloys include, but are not limited to cobalt-chromium-nickel alloys, titanium-vanadium alloys, stainless steel and other materials that are well known for use in the manufacture of implantable bone prostheses.

It is understood that for some casting shapes the mold may be filled with a metal or metal alloy powder rather than a molten metal or metal alloy. In such an application heat is subsequently applied to solidify the casting according to well known techniques.

After a casting, the implantable bone prostheses are removed from the casting mold(s) as finished product. Where the casting mold is green, i.e., unfired, it is readily crumbled and destroyed and separated from the prostheses. A fired ceramic casting mold may be provided with one or more sections which are joined to form the prostheses and that can be separated as needed to remove the finished product. As noted above, ultrasonic cleaning and selective etching may used to remove all residues of the mold from the cast metal article.

Although not specifically described herein it is understood that the cast articles may be manufactured according to the process of this invention with desired surface textures that can also be prepared by 3-D printing techniques.

The implantable article of the invention can also be manufactured by direct 3-D printing of the metal component.

The foregoing description of methods of manufacture of illustrative embodiments is presented to indicate the range of constructions to which the invention applies. Variations in the physical architecture and mold processes of the present invention will be apparent to those skilled art based upon the disclosure herein, and such variations are considered to be within the scope of the invention in which patent rights are asserted, as set forth in the claims appended hereto.

What is claimed is:

1. An implantable article for placement within a joint space, comprising a unitary articulation member having an articulation surface and an opposed, bone-engaging surface, the articulation member having
   one or more primary internal passageways extending internally within the member from a fluid communication inlet port disposed on a surface of the article adjacent to the joint space, and means for communicating fluid from the primary internal passageways to the articulation surface, the primary passageways and means for communicating being able to convey synovial fluid from within the joint space to the articulation surface to provide lubrication between the articulation member and another articulation component of an artificial joint.

2. The implantable article of claim 1 wherein the means for communicating is a fluid communication outlet port of the primary internal passageway that is disposed on the articulation surface of the articulation member.

3. The implantable article of claim 1 wherein the means for communicating comprises one or more secondary internal passageways, each extending from one of the primary internal passageways to a fluid communication outlet port disposed on the articulation surface of the articulation member.

4. The implantable article of claim 1 wherein the primary internal passageways have smooth internal walls and are spatially oriented within the articulation member so as to allow smooth and continuous flow of fluid therethrough.

5. The implantable article of claim 4 wherein the primary internal passageways extend within the member in an orientation substantially parallel to at least one of the articulation surface or the bone contacting surface.

6. The implantable article of claim 4 wherein the articulation member is a cast metal article having as-cast primary internal passageways.

7. The implantable article of claim 4 wherein the articulation member is formed of a castable, biologically compatible material selected from the group consisting of metals and ceramics.

8. The implantable article of claim 4 wherein the articulation member is formed of metals selected from the group consisting of cobalt-chromium-nickel alloy, titanium-vanadium alloy, and stainless steel.

9. The implantable article of claim 4 wherein the articulation member is formed of ceramics selected from the group consisting of alumina, zirconia, silicon nitride, silica, silicon carbide, and mixtures thereof.

10. The article of claim 7 wherein the articulation member is an acetabular shell.

11. The implantable article of claim 7 wherein the articulation member is a femoral head.

12. The implantable article of claim 7 wherein the articulation member is a knee tibial.

13. The implantable article of claim 7 wherein the articulation member is a knee femoral.

14. The article of claim 1 wherein the diameter of the primary internal passageways is in the range of about 0.005 to 0.100 inch.

15. The article of claim 3 wherein the diameter of the secondary internal passageways is in the range of about 0.005 to 0.100 inch.

16. An implantable hip joint comprising:
a hip femoral component having a distal, elongate shaft and a proximal neck region;
a hemispherical femoral head component able to be secured to the neck, the head component having a smooth external articulation surface;
an acetabular shell having an internal bone-engaging surface and an external, cup-like articulation surface for receiving the femoral head component, the acetabular shell having one or more primary internal passageways and means for communicating synovial fluid from the primary internal passageway to the articulation surface, the primary internal passageways extending internally within the acetabular shell from a fluid communication inlet port disposed on an external surface of the acetabular shell adjacent to a joint space.

17. The hip joint of claim 16 wherein the means for communicating comprises one or more secondary internal passageways, each extending from one of the primary internal passageways to a fluid communication outlet port disposed on the articulation surface.

18. The hip joint of claim 17 wherein the acetabular shell is a cast metal article having as-cast primary internal passageways.

19. The hip joint of claim 17 wherein the cup-like articulation surface of the acetabular shell is formed of a biologically compatible material selected from the group consisting of metals and ceramics.

20. The implantable article of claim 17 wherein the articulation member is formed of metals selected from the group consisting of cobalt-chromium-nickel alloy, titanium-vanadium alloy, and stainless steel.

21. The implantable article of claim 17 wherein the articulation member is formed of ceramics selected from the group consisting of alumina, zirconia, silicon nitride, silica, silicon carbide, and mixtures thereof.

22. The hip joint of claim 16 wherein the articulation surface of the femoral head component is formed of a biologically compatible material selected from the group consisting of metals and ceramics.

23. The hip joint of claim 16 wherein the primary internal passageways have a diameter in the range of about 0.005 to 0.100 inch.

24. The hip joint of claim 17 wherein the secondary internal passageways have a diameter in the range of about 0.005 to 0.100 inch.

25. An implantable article comprising a unitary articulation member having an articulation surface and an opposed, bone contacting surface, the articulation member having
one or more synovial fluid communicating passageways extending internally within the member from a fluid communication inlet port disposed on a surface of the article adjacent a joint space, and
one or more secondary internal passageways, each extending from a fluid communication port on one of the primary internal passageways to a fluid communication outlet port disposed on the articulation surface, the primary and secondary internal passageways being able to convey synovial fluid from within the joint space to the articulation surface to provide lubrication between the articulation member and another articulation component of an artificial joint.

* * * * *